(12) United States Patent
Srinivasan et al.

(10) Patent No.: US 8,394,027 B2
(45) Date of Patent: Mar. 12, 2013

(54) MULTI-PLANE/MULTI-SLICE PROCESSING FOR 2-D FLOW IMAGING IN MEDICAL DIAGNOSTIC ULTRASOUND

(75) Inventors: Seshadri Srinivasan, Santa Clara, CA (US); Kutay F. Ustuner, Mountain View, CA (US); Ismayil M. Guracar, Redwood City, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 321 days.

(21) Appl. No.: 12/422,079

(22) Filed: Apr. 10, 2009

(65) Prior Publication Data

US 2009/0306513 A1   Dec. 10, 2009

Related U.S. Application Data

(60) Provisional application No. 61/059,681, filed on Jun. 6, 2008.

(51) Int. Cl.
*A61B 8/00* (2006.01)
(52) U.S. Cl. ......... 600/454; 600/437; 600/453; 382/128
(58) Field of Classification Search .................. 600/407, 600/437, 443, 447, 456; 702/159; 382/128
See application file for complete search history.

(56) References Cited

U.S. PATENT DOCUMENTS

| | | | |
|---|---|---|---|
| 6,350,241 B1 | 2/2002 | Lifshitz | |
| 6,464,638 B1 * | 10/2002 | Adams et al. | 600/443 |
| 6,535,835 B1 * | 3/2003 | Rubin et al. | 702/159 |
| 6,685,641 B2 | 2/2004 | Liu | |
| 6,733,453 B2 | 5/2004 | Freiburger et al. | |
| 6,859,659 B1 | 2/2005 | Jensen | |
| 7,097,619 B2 * | 8/2006 | Von Behren et al. | 600/447 |
| 2003/0114756 A1 * | 6/2003 | Li | 600/437 |
| 2006/0039589 A1 | 2/2006 | Hall et al. | |
| 2006/0098853 A1 * | 5/2006 | Roundhill et al. | 382/128 |
| 2007/0255136 A1 * | 11/2007 | Kristofferson et al. | 600/437 |
| 2008/0097212 A1 * | 4/2008 | Srinivasan et al. | 600/453 |

* cited by examiner

*Primary Examiner* — James Kish
*Assistant Examiner* — Michael N Fisher

(57) ABSTRACT

A volumetric method for 2-D flow imaging is provided in medical diagnostic ultrasound. Flow data for a volume is acquired. For more rapid acquisition, broad beam transmission and reception along many scan lines distributed in the volume is used. The volumetric flow data is filtered, such as by calculating statistical information, to generate a planar/2-D flow image. The statistical information from the three-dimensional flow data is used to determine the display values for the flow imaging.

17 Claims, 2 Drawing Sheets

MULTI-PLANE/MULTI-SLICE PROCESSING FOR 2-D FLOW IMAGING IN MEDICAL DIAGNOSTIC ULTRASOUND

CROSS-REFERENCE TO RELATED APPLICATIONS

The present patent document claims the benefit of the filing date under 35 U.S.C. §119(e) of Provisional U.S. Patent Application Ser. No. 61/059,681, filed Jun. 6, 2008, which is hereby incorporated by reference.

BACKGROUND

This present invention relates to medical diagnostic ultrasound. In particular, two dimensional flow imaging is provided.

Flow imaging is performed with color Doppler processes. The Doppler effect is used to estimate velocity, energy and/or variance of flow. The flow information is mapped to a color for imaging.

To image flow in a patient, the user positions the transducer at a desired location. Due to the sensitivity of the flow to the angle of insonification, the transducer is repositioned to identify the location with the best image. However, this repositioning may result in a longer examination.

Flow imaging includes other variables. The user adjusts the overall gain and depth gains and velocity scale settings. Proper settings may improve the flow sensitivity and fill-in. However, even images acquired with proper settings may have flow holes or insufficient sensitivity.

SUMMARY OF THE INVENTION

By way of introduction, the preferred embodiments described below include a method, system, computer readable medium, and instructions for 2-D flow imaging in medical diagnostic ultrasound. Flow data for a volume is acquired. For more rapid acquisition, broad beam transmission and simultaneous reception along many scan lines distributed in the volume is used. The flow data for the volume is filtered, such as by calculating statistical information. The statistical information is used to determine the display values for the flow imaging. The display value for each location in the image may be based on data in a surrounding three-dimensional region.

In a two-dimensional imaging aspect, a method is provided for two-dimensional flow imaging in medical diagnostic ultrasound. Flow data representing a plurality of different planes in an object is acquired. Flow values for a first plane are determined as a function of the flow data for the plurality of different planes. A flow image representing flow in a two-dimensional region corresponding to the first plane is generated as a function of the flow values.

In a two-dimensional imaging aspect, a computer readable storage medium has stored therein data representing instructions executable by a programmed processor for flow imaging in medical diagnostic ultrasound. The storage medium includes instructions for acquiring, in response to one transmission, spatial samples of an object, the spatial samples distributed in a volume including at least parts of multiple slices, repeating the acquiring at different times, estimating color Doppler parameter values from the spatial samples acquired at the different times, the color Doppler parameter values representing the at least parts of the multiple slices, combining the color Doppler parameter values for the multiple slices into a two-dimensional representation, and generating an image as a function of the combined color Doppler parameter values.

In another aspect, a system is provided for flow imaging in medical diagnostic ultrasound. A beamformer is operable to scan with a transducer. A Doppler estimator is operable to estimate Doppler data for a volume from information obtained by the scan. A processor is operable to determine a display value for each location in an image from Doppler data distributed three-dimensionally in an at least three-by-three-by-three voxel region in the volume. A display is operable to display the image.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF SPECIFIC EMBODIMENTS

The color Doppler fill-in, sensitivity, and signal-to-noise ratio (SNR) for two-dimensional (2D) flow imaging may be improved by using simultaneous acquisition of multiple thin-slices or volume data. For two-dimensional imaging, the image may be displayed as a 2D slice through some combination of the data in the slices. Acquisition of thin slices may be performed using multi-dimensional array probes (1.5, 1.75D or 2D) or 1D arrays with mechanical steering. Volumetric processing of the thin slices through spatial filtering improves SNR and signal sensitivity. For 2D imaging, combination of the color information in the thin-slices may use the local and/or regional image statistics, such as mean, mix, max, median, and spatial variance. Using volume information may more likely provide a sufficient image, minimizing the time spent repositioning the transducer and improving workflow.

In one two-dimensional imaging example embodiment, color Doppler imaging is performed with simultaneous acquisition of spatial samples of an object in a volume along multiple slices using broad beam transmission. Temporal samples are acquired along the same set of slices. Color Doppler parameters are estimated from the temporal samples. Estimates from the multiple slices are combined into a single slice (collapse of dimensionality). The combination may use neighborhood statistics (e.g., parameters from a surrounding volume). The color Doppler imaging may be combined with B-mode imaging.

Figure 1:
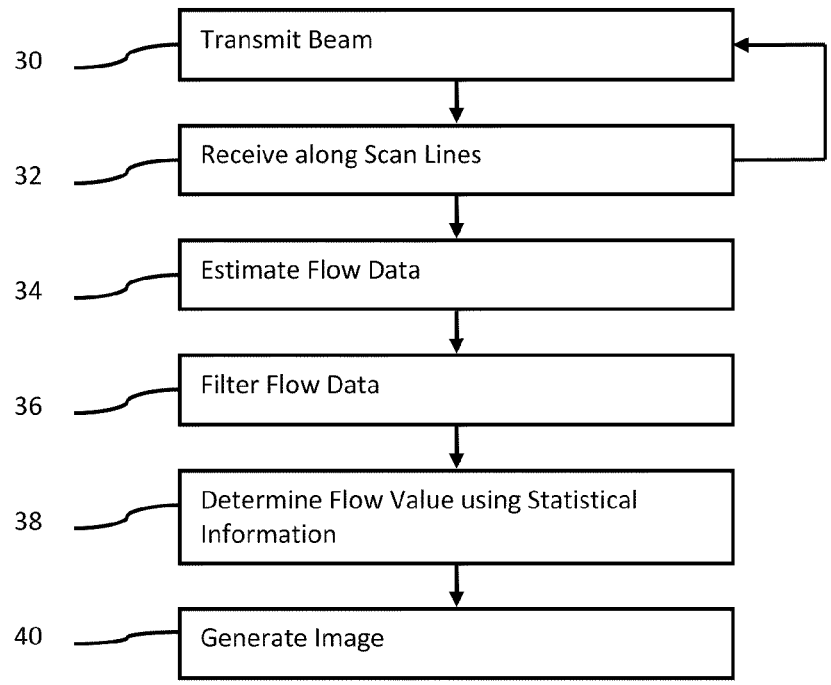
FIG. 1 is a flow chart of one embodiment of a method for flow imaging.

FIG. 1 shows a method for flow imaging in medical diagnostic ultrasound. The method is performed by the system 10 of FIG. 4 or a different system according to various embodiments. The acts of FIG. 1 are performed in the order shown or a different order according to various embodiments. Additional, different or fewer acts than shown in FIG. 1 may be used. For example, act 36 is not provided in a specific embodiment. The acts of FIG. 1 described below may be implemented in different ways. At least one example embodiment is provided below, but other embodiments are possible.

Acts 30 and 32 correspond to acquiring flow data. The reception of act 32 occurs in response to the transmissions of act 30. The acts 30 and 32 are repeated until the desired volume is scanned.

The volume is scanned along different planes or other distribution of scan lines within the volume. The scanned volume is an interior of an object, such as a patient. Scanning the volume provides data representing the volume, such as representing a plurality of different planes in the object. The data representing the volume is formed from spatial sampling of the object. The spatial samples are for locations distributed in an acoustic sampling grid in the volume. Where the acoustic sampling grid includes planar arrangements of samples, the spatial samples of the object include samples of multiple planes or slices.

In act 30, acquisition of the spatial samples of the object is started with a transmission. A beam of acoustic energy is transmitted. The beam is electrically and/or mechanically focused in azimuth and/or elevation. One or more beams are transmitted at a same time. Each beam is for one scan line.

In an alternative embodiment, a broad beam is transmitted. The beam is broad or wide enough to cause echoes from locations for spatial samples distributed in a plane or volume. For example, the broad beam has 6 dB down borders (relative to its peak) surrounding scan lines in at least parts of multiple slices. As another example, the broad beam is sufficiently wide to insonify at least sixteen distinct receive lines for receiving spatial samples along the receive lines. Any number of receive lines may be within a given transmitted beam, such as 8×8, 8×5, 7×6 or other array of receive lines in a volume. For scanning along different planes, one dimension of the receive line grouping defines the number of planes insonified by a given transmit beam. In the 8×5 array of receive lines example, eight receive lines in each of five adjacent planes are within the acoustic envelope of the transmit beam. For two-dimensional imaging, the five adjacent planes are spaced apart in elevation.

To generate a broad transmit beam, a single element of a transducer is excited, generating a spherical (or cylindrical) wavefront, diverging as it propagates. Alternatively, a convex delay profile is applied to a transmit array such that a diverging wavefront (a defocused beam) emanates seemingly from a virtual element behind the transducer. If the virtual element is modeled at an infinite distance from the transducer, a plane wave (an unfocused beam) is generated. Where the virtual transmit element is closer to the transducer, the resulting broad transmit beam becomes more diverging and less focused. Alternatively, the transducer is focused shallower than the object creating a real "point" source in between the transducer and the object. The wavefront converges before the object and diverges within the object. The transmit apodization profile and spectral shape of the excitation pulse may be chosen to further shape the transmit beam. In other embodiments, the focal region is positioned beyond the region of interest either within or outside of the patient. The beam may be converging, but converges only a limited amount over the region of interest.

Each broad transmit beam covers at least a two dimensional region. For a plane wave, the broad transmit beam is about as wide as the active transmit aperture. For a diverging wave associated with a real or a virtual transmit element behind the transducer, the broad transmit beam is wider than the active transmit aperture for deeper depths.

For simultaneous acquisition or reception, different receive beams are formed in response to a same transmit beam. Simultaneous may or may not include parallel beamformation. For example, data responsive to one transmit is sequentially processed to form different receive beams. Since the data is responsive to the same transmit beam, the data is acquired simultaneously. The breadth of the transmit beam allows for simultaneous acquisition or reception as compared to sequential acquisition by firing a transmit beam along one line, receiving along that line, then firing a transmit beam along another line, and then receiving along that other line. Multiple simultaneous acquisitions may be used to scan a volume, such as providing simultaneous acquisition for different sub-volumes.

The color pulses are transmitted with a broad-beamwidth in elevation using any type of transducer array. For matrix array probes (e.g., 2D array of elements), a plane-wave source, a virtual point source, or a bi-cylindrical transmit-focus (different elevation and azimuth focal depths) is used. For 1.5D array probes, the focal position is deeper than the region of interest or scan region along one or more dimensions, such as the elevation dimension. For mechanically steered 3D probes (e.g., a wobbler having a one-dimensional array that is mechanically oscillated), conventional transmit focusing may be used or a broad beam is generated along one dimension but not another.

In act 32, spatial samples along one or more scan lines are received. Where the transmit beam insonifies just one receive scan line, then samples along that scan line are received. Where the transmit beam insonifies multiple scan lines, then samples along the multiple scan lines are received. For example, receive beamforming is performed along at least sixteen distinct receive lines in response to one broad transmit beam. To generate the samples for different receive beams, parallel receive beamformation is performed so that the different receive beams are sampled at a same time. For example, a system may be capable of forming tens or hundreds of receive beams in parallel. Alternatively, signals received from the elements are stored and sequentially processed.

Spatial samples are acquired for a plurality of receive lines in response to one transmit beam and/or in response to sequential transmit beams. The receive lines are in different planes or have other distribution in the volume rather than along a single plane. The multiple planes have different positions, such as being parallel. The planes may intersect or may be closer at one end than another end. The planes are spaced apart in elevation along at least one depth. Each plane is bounded in the azimuth and range dimensions of the scan.

Using broad beam transmission, spatial samples for multiple thin slices may be simultaneously formed using dynamic receive focusing (e.g., delay and/or phase adjust and sum). Alternatively, Fourier or other processing may be used to form the spatial samples.

As represented by the feedback arrow from act 32 to act 30, the scanning may be performed a plurality of times. The acts are repeated to scan different portions of the region of interest. Alternatively, performing acts 30 and 32 once acquires the data for the entire region of interest.

The complete region of interest is scanned at different times. Scanning at different times acquires spatial samples associated with flow. Any now known or later developed pulse sequences may be used. A sequence of at least two (flow sample count) transmissions is provided along each scan line.

Any pulse repetition frequency, flow sample count, and pulse repetition interval may be used. The echo responses to the transmissions of the sequence are used to estimate velocity, energy (power), and/or variance at a given time. The transmissions along one line(s) may be interleaved with transmissions along another line(s). With or without interleaving, the spatial samples for a given time are acquired using transmissions from different times. The estimates from different scan lines may be acquired sequentially, but rapidly enough to represent a same time from a user perspective. Multiple scans are performed to acquire estimates for different times.

The received spatial samples may be clutter filtered. The signals for each spatial location are transferred from buffers or a memory (e.g., corner turning memory) to a filter. The filter pass band, rise time, rejection band, and other characteristics are set to reduce the contribution from undesired information. For example, the samples are filtered to remove or reduce information from slowly moving or non-moving tissue, leaving signals from moving fluid. As another example, signals from tissue remain, and signals from more rapidly moving fluid are reduced. In other examples, signals associated with motion remain, but signals associated with possible noise or lack of motion are removed. Any now known or later developed clutter filtering may be used.

The clutter filtering is of signals in the pulse sequence for estimating motion at a given time. A given signal may be used for estimates representing different times, such as associated with a moving window for clutter filtering and estimation. Different filter outputs are used to estimate motion for a location at different times.

In act 34, flow data is generated from the spatial samples. Any flow data may be generated, such as velocity, energy (power), and/or variance. Doppler processing, such as autocorrelation, may be used. In other embodiments, temporal correlation may be used. Another process may be used to estimate the flow data. Color Doppler parameter values (e.g., velocity, energy, or variance values) are estimated from the spatial samples acquired at different times. Color is used to distinguish from spectral Doppler imaging, where the power spectrum for a range gate is estimated. The change in frequency between two samples for the same location at different times indicates the velocity. A sequence of more than two samples may be used to estimate the color Doppler parameter values. Estimates are formed for different groupings of received signals, such as completely separate or independent groupings or overlapping groupings. The estimates for each grouping represent the spatial location at a given time. Multiple frames of flow data may be acquired to represent the region of interest at different times.

The estimation is performed for spatial locations in the volume. For example, velocities for the different planes are estimated from echoes responsive to the scanning. The color Doppler parameter values from the scan of the entire region of interest represent the response along multiple slices or planes. Flow data is provided for at least two planes.

The estimates may be thresholded. Thresholds are applied to the velocities. For example, a low velocity threshold is applied. Velocities below the threshold are removed or set to another value, such as zero. As another example, where the energy is below a threshold, the velocity value for the same spatial location is removed or set to another value, such as zero. Alternatively, the estimated velocities are used without thresholding.

In act 36, the flow data is filtered. The filtering is spatial filtering along one, two, or three-dimensions. For example, two-dimensional filtering is performed in each plane. As another example, one-dimensional filtering is performed across planes (e.g., filtering across the elevation dimension). In another example, a three-dimensional kernel is applied. Any spatial filter may be used, such as 5-7 tap filter in at least one dimension.

Any filtering may be used, such as low pass or band pass filtering. Spatial filtering may limit noise and/or speckle. Other noise reduction and/or speckle filtering may be used. Adaptive filtering may be used. In alternative embodiments, filtering is not provided, is provided prior to thresholding, or is provided before estimation.

In act 38, flow values for at least one plane are determined. For two-dimensional imaging, the flow values for one plane are determined. The plane is the center or middle plane, but may be an edge or other scan plane. The plane for imaging may be an arbitrary plane different than the planes used for the spatial sampling. Flow values for other planes may not be determined. The flow values for the imaging plane are used for generating a flow image, such as a color flow or color Doppler image. In one two-dimensional imaging embodiment, the scanning is of elevation spaced planes, and the flow values are determined/displayed for one of the planes and not others. The flow data from the different planes are used to determine flow values for just one plane. The view direction is always normal to the one plane. To image a different location, the user moves the transducer rather than selecting a different viewing direction for rendering.

The flow values for a given plane are determined as a function of the flow data for multiple planes. For example, the flow values for a center or single plane are determined from flow data for all or a closest sub-set of planes. A kernel or window defines the spatial extent of flow data used to determine a given flow value. The kernel has at least an elevation extent for two-dimensional imaging. In one embodiment, the kernel is three-dimensional, such as defining a 7×7×7 volume (specified in axial×lateral×elevation pixel units). The flow value for a given location is determined by the flow data for that location and the flow data within the kernel centered over that location. To determine the flow value for another location, the kernel is spatially shifted. A three-dimensional kernel may reduce noise, speckle, and holes in a resulting flow image, even for a two-dimensional image generated based on just one of the planes.

The flow data (e.g., color Doppler parameter values) for the multiple slices are combined into a two-dimensional representation. Any function may be applied to combine the data in the kernel or window. For each of a plurality of locations in the first plane, a statistic is calculated from the flow data for a surrounding three-dimensional region. A statistic is computed from the flow data of the thin-slices, such as the mean, weighted-mean, maximum, weighted-max, or standard deviation. For example, $stat(i,j,k)=\max_k(Vel(i,j,k))$ or $stat(i,j,k)=\max_k(Ene(i,j,k))$, wherein i, j, and k index three dimensions and Vel represents velocity and Ene represents energy. As other examples, $stat(i,j,k)=\mean_k(Vel(i,j,k))$ or $stat(i,j,k)=\mean_k(Ene(i,j,k))$; $stat(i,j,k)=\std_k(Vel(i,j,k))$ or $stat(i,j,k)=\std_k(Ene(i,j,k))$, where std is the standard deviation; $stat(i,j,k)=\max_k(spat\_filt_k(Vel(i,j,k)))$ or $stat(i,j,k)=\max_k(spat\_filt_k(Ene(i,j,k)))$, where spat_filt is a weight function. Any weight function may be used, such as more heavily weighting values in a same elevation (e.g., k) position and/or closer to the center of the kernel, and/or weights providing a low pass filter function.

The flow value for a given location is determined as a function of the statistic for that location. For example, the color Doppler parameter values are set to be the statistic, a weighted sum of the flow data for the location and the statistic, the flow data or another value depending on a threshold applied to the statistic, or combinations thereof. For example, the flow value is Vel(i,j,k)=stat(i,j,k) or Ene(i,j,k)=stat(i,j,k); Vel(i,j,k)=Vel(I,j,k) if (stat(i,j,k)>Threshold) or Ene(i,j,k)= Ene(I,j,k) if (stat(i,j,k)>threshold), otherwise Vel or Ene=0; or Vel(i,j,k)=a*Vel(i,j,k)+(1−a)*stat(i,j,k) or Ene(i,j,k)= a*Ene(i,j,k)+(1−a)*stat(i,j,k), where a is any weight function. Other functions of the statistic may be used.

In one embodiment, the statistic is directional. For example, the weights applied in a weighted mean function have an orientation pattern. As another example, flow data within the kernel along a direction of flow are more heavily weighted. The orientation information is used to enhance the flow data along the flow orientation. Flow data along the flow orientation more heavily contributes to the flow value. The orientation may be used to angle correct the flow data. The angle correction may be one, two, or three-dimensional. Locations with low or no flow data surrounded by flow on both sides along the direction of flow may be identified and a non-zero flow value extrapolated or interpolated. This directional statistic may fill-in holes in the flow data (e.g., remove low or zero value flow) and improve color sensitivity.

In one embodiment, a coarse or other orientation of flow is determined in a local neighborhood. The local neighborhood is the same, larger, or smaller as the kernel applied to calculate the statistic. Since the vessel may not be straight throughout the color region of interest, the different orientations of the vessel are determined as a function of spatial location. A gradient is calculated in three directions. The direction with the maximum gradient is considered the direction of flow. In alternative embodiments, the orientation is determined for the entire region of interest.

Finer orientation calculation may be used. Any technique to determine vessel orientation may be used, such as a region thinning, boundary detection, peak velocity, curve fitting, or center of mass. In one embodiment, a frame of velocity values is decimated by any desired amount. Decimation may reduce calculation. No or any amount of decimation may be provided, according to specific embodiments. The decimated frame of data is thresholded (using energy and/or velocity thresholds) and binarized. For example, an energy threshold is applied. Values above the threshold are set to one and values below are set to zero. Binarizing may identify locations more likely associated with the flow in the vessel. Three or more discrete values may be used in alternative embodiments, such as to provide for weighted identification of the vessel orientation. A morphological process, such as skeletonization, is applied to the binary image. The morphological process identifies the vessel orientation ($\phi_{vessel}$) at different locations along the vessel.

Another directional statistic is the direction of the flow border. Any border detection may be used. The flow data and/or B-mode data may be used to determine the location of the border. For example, three-dimensional gradients are calculated for energy data. The gradients are binarized to identify the location of the border. A curve fitting, low pass filtering or other information may be used to smooth the border. The kernel weights are applied as a function of proximity to the border. For locations near or on the border, the weights may be altered so that flow within the border contributes more heavily than the lack of flow outside the border. Alternatively or additionally, the thresholds applied to the flow data may adapt to the border. The thresholds are higher for interior regions and lower for border regions since flow may be naturally lower at the border. Adapting the thresholds to distinguish flow from non-flow may result in better identification of the flow region, providing larger, more accurate, flow regions than without the adaptation.

Other directional statistics may be used. Combinations of the statistics may be used.

In act 40, a 2-D image is generated. The image represents the 2-D flow along a plane in the volume of the scanned object. The flow image represents flow in a two-dimensional region corresponding to one of the scan planes or an arbitrary plane through the volume. For example, the flow values are determined for each location along an arbitrary plane and used for generating the image, and not for other locations.

A color image is generated. For example, a velocity image is generated as a function of the flow values for the plane. The flow values are mapped to a color. Alternatively, a gray scale mapping is used. The image represents velocity, energy, and/or variance. Each pixel or color value is based on the flow data or color Doppler parameter values formed from flow data of multiple planes or volume locations. The two-dimensional image may be formed without rendering.

The color image may be overlaid on or combined with a B-mode image. Color values are displayed for the regions of interest and not for other spatial locations. B-mode data is displayed at other locations. For example, flow values are used for locations with a threshold level of flow information, and B-mode values are used at other locations. The two-dimensional B-mode information and the combined color Doppler parameter values are represented at different locations within the image. Both the B-mode and flow values represent a same plane or two-dimensional region of the patient.

Figures 2A, 2B:
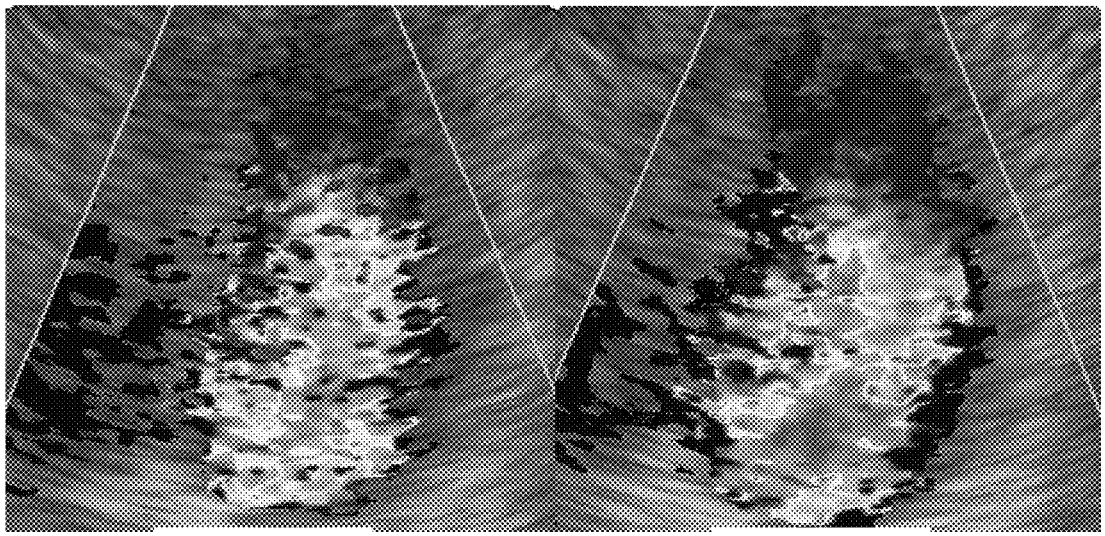
FIGS. 2A and 3A are example flow images generated using conventional flow imaging.
FIGS. 2B and 3B are example flow images generated using the method of FIG. 1.
Figures 3A, 3B:
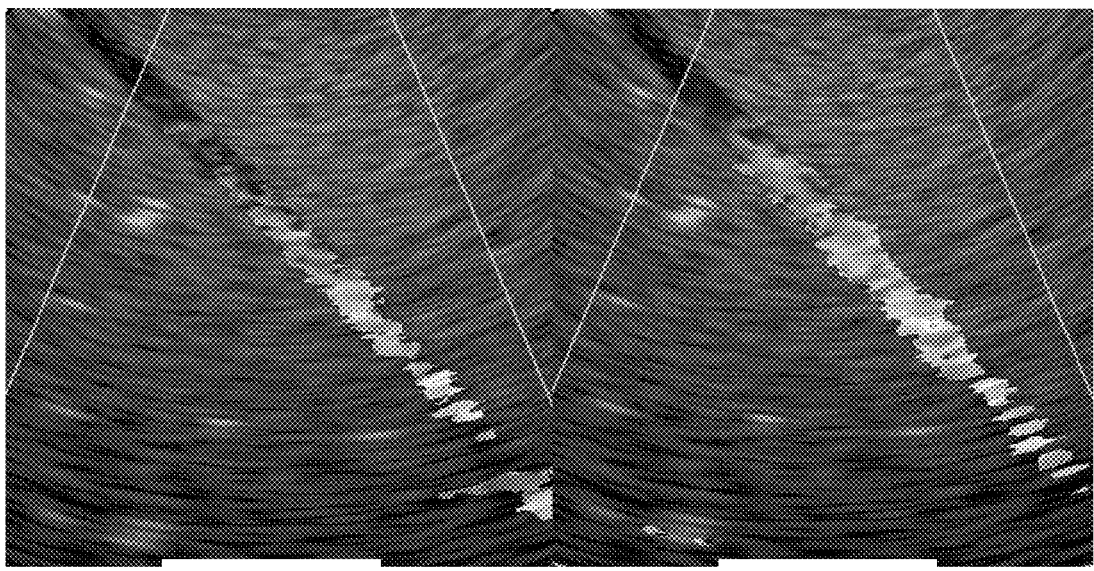

FIGS. 2A and 2B represent the heart in a cardiac image. FIGS. 3A and 3B represent a phantom. FIGS. 2A and 3A show combined color Doppler velocity and B-mode images generated by a conventional two-dimensional scan. FIGS. 2B and 3B show the larger, more accurate region of flow, fewer holes (e.g., more fill-in), less speckle, and less noise resulting from two-dimensional imaging using statistics from a surrounding three-dimensional volume, according to specific embodiments of the invention. For FIGS. 2B and 3B, the region was scanned with broad beam transmit with eight receive lines in azimuth and five receive lines in elevation per broad transmit beam, a statistic kernel of 7×7×5 (axial×lateral×elevation), where the flow value for the image is set to the mean velocity.

Figure 4:
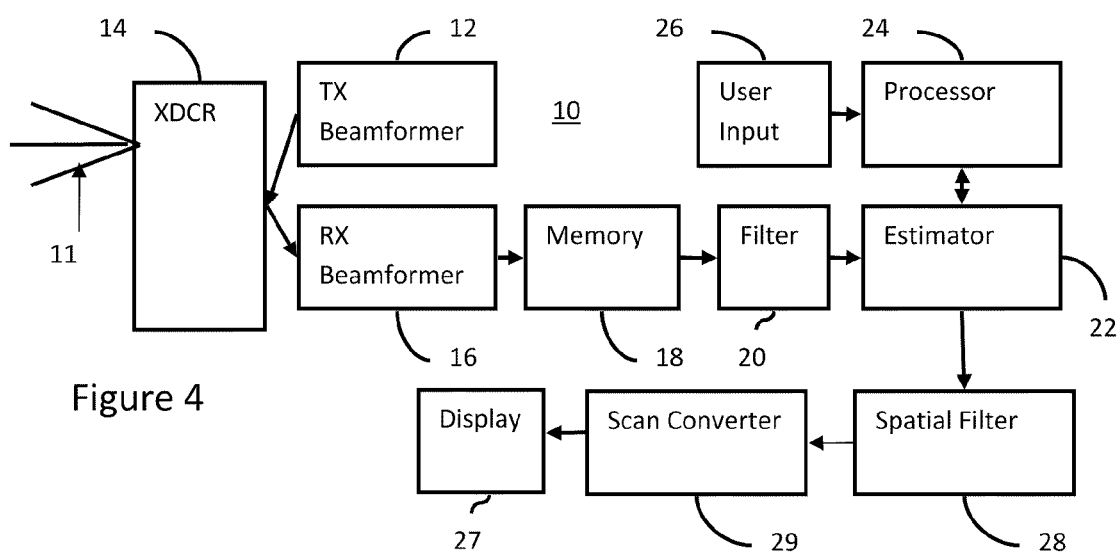
FIG. 4 is a block diagram of one embodiment of a system for flow imaging.

FIG. 4 shows one embodiment of a system 10 for flow imaging in medical diagnostic ultrasound. The system 10 includes a transmit beamformer 12, a transducer 14, a receive beamformer 16, a memory 18, a filter 20, a flow estimator 22, a spatial filter 28, a scan converter 29, a processor 24, a user input 26, and a display 27. Additional, different or fewer components may be provided. For example, the system includes the flow estimator 22 and processor 24 without the front-end components such as the transmit and receive beamformers 12, 16. In one embodiment, the system 10 is a medical diagnostic ultrasound system. In an alternative embodiment, the system 10 is a computer or workstation. In yet another embodiment, the flow estimator 22 is part of a medical diagnostic ultrasound system or other medical imaging system, and the processor 24 is part of a separate workstation or remote system.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, a wobbler array, combinations thereof, or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit and receive beamformers 12, 16 are a beamformer for scanning with the transducer 14. The transmit beamformer 12, using the transducer 14, transmits one or more beams to scan a region. Vector®, sector, linear or other scan formats may be used. In one embodiment, the transmit beamformer 12 transmits beams sufficiently large to cover at least sixteen distinct receive lines, and the receive beamformer 16 receives along these distinct receive lines in response to the transmit beam. Use of the broad beam transmit and parallel receive beamforming along tens or hundreds of receive lines allows for real-time scanning of multiple slices or a volume. The receive lines and/or transmit beams are distributed in the volume, such as the receive lines for one transmit being in at least two different planes. The receive beamformer 16 samples the receive beams at different depths. Sampling the same location at different times obtains a sequence for flow estimation.

In one embodiment, the transmit beamformer 12 is a processor, delay, filter, waveform generator, memory, phase rotator, digital-to-analog converter, amplifier, combinations thereof or any other now known or later developed transmit beamformer components. In one embodiment, the transmit beamformer 12 digitally generates envelope samples. Using filtering, delays, phase rotation, digital-to-analog conversion and amplification, the desired transmit waveform is generated. Other waveform generators may be used, such as switching pursers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal or other waveforms of a desired center frequency or frequency band with one, multiple or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles and combinations thereof. A transmit beam focus is generated based on these beamforming parameters.

The receive beamformer 16 is a preamplifier, filter, phase rotator, delay, summer, base band filter, processor, buffers, memory, combinations thereof or other now known or later developed receive beamformer components. The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. In one embodiment, the beamform summer is operable to sum in-phase and quadrature channel data in a complex manner such that phase information is maintained for the formed beam. Alternatively, the beamform summer sums data amplitudes or intensities without maintaining the phase information.

The receive beamformer 16 is operable to form receive beams in response to the transmit beams. For example, the receive beamformer 16 receives one, two, or more (e.g., 30, 40, or 50) receive beams in response to each transmit beam. The receive beams are collinear, parallel and offset, or non-parallel with the corresponding transmit beams. The receive beamformer 16 outputs spatial samples representing different spatial locations of a scanned region. Once the channel data is beamformed or otherwise combined to represent spatial locations along the scan lines 11, the data is converted from the channel domain to the image data domain. The phase rotators, delays, and/or summers may be repeated for parallel receive beamformation. One or more of the parallel receive beamformers may share parts of channels, such as sharing initial amplification.

For imaging motion, such as tissue motion or fluid velocity, multiple transmissions and corresponding receptions are performed for a substantially same spatial location. Phase changes between the different receive events indicate the velocity of the tissue or fluid. A velocity sample group corresponds to multiple transmissions for each of a plurality of scan lines 11. The number of times a substantially same spatial location, such as a scan line 11, is scanned within a velocity sample group is the velocity sample count. The transmissions for different scan lines 11, different velocity sample groupings or different types of imaging may be interleaved. The amount of time between transmissions to a substantially same scan line 11 within the velocity sample count is the pulse repetition interval or pulse repetition frequency. Pulse repetition interval is used herein, but includes the pulse repetition frequency.

The memory 18 is video random access memory, random access memory, removable media (e.g. diskette or compact disc), hard drive, database, corner turning memory or other memory device for storing data or video information. In one embodiment, the memory 18 is a corner turning memory of a motion parameter estimation path. The memory 18 is operable to store signals responsive to multiple transmissions along a substantially same scan line. The memory 22 is operable to store ultrasound data formatted in an acoustic grid, a Cartesian grid, both a Cartesian coordinate grid and an acoustic grid, or ultrasound data representing a volume in a 3D grid.

The filter 20 is a clutter filter, finite impulse response filter, infinite impulse response filter, analog filter, digital filter, combinations thereof or other now known or later developed filter. In one embodiment, the filter 20 includes a mixer to shift signals to baseband and a programmable low pass filter response for removing or minimizing information at frequencies away from the baseband. In other embodiments, the filter 20 is a low pass, high pass or band pass filter. The filter 20 identifies velocity information from slower moving tissue as opposed to fluids or alternatively reduces the influence of data from tissue while maintaining velocity information from fluids. The filter 20 has a set response or may be programmed, such as altering operation as a function of signal feedback or other adaptive process. In yet another embodiment, the memory 18 and/or the filter 20 are part of the flow estimator 22.

The flow or Doppler estimator 22 is a Doppler processor or cross-correlation processor for estimating the flow data. In alternative embodiments, another device now known or later developed for estimating velocity, energy, and/or variance from any or various input data may be provided. The flow estimator 22 receives a plurality of signals associated with a substantially same location at different times and estimates a Doppler shift frequency, based on a change or an average change in phase between consecutive signals from the same location. Velocity is calculated from the Doppler shift frequency. Alternatively, the Doppler shift frequency is used as a velocity. The energy and variance may also be calculated.

Flow data (e.g., velocity, energy, or variance) is estimated for spatial locations in the scan volume from the beamformed scan samples. For example, the flow data represents a plurality of different planes in the volume.

The flow estimator 22 may apply one or more thresholds to identify sufficient motion information. For example, velocity and/or energy thresholding for identifying velocities is used. In alternative embodiments, a separate processor or filter applies thresholds.

The spatial filter 28 is a finite impulse response filter, infinite impulse response filter, analog filter, digital filter, combinations thereof or other now known or later developed filter. In one embodiment, the spatial filter 28 includes a mixer to shift signals to baseband and a programmable low pass filter response for removing or minimizing information at frequencies away from the baseband. In other embodiments, the spatial filter 28 is a low pass, high pass or band pass filter. The spatial filter 28 may include a memory for storing data representing different spatial locations.

The scan converter 29 converts data from a polar coordinate format to a Cartesian coordinate format. Interpolation, nearest neighbor, or other conversion may be used. The scan converter 29 may include a look-up table or processor for converting motion estimates to color (e.g., RGB).

The user input 26 is a keyboard, buttons, joystick, trackball, mouse, sliders, touch pad, combinations thereof or other now known or later developed input device. The user input 26 provides signals to the processor 24 or other components of the system 10 in response to user activation. For example, the signals from the user input 26 control configuration of the system 10 for velocity imaging. The user input 26 may be used to designate or assist in processor based designation of a region of interest.

The display 27 is a CRT, LCD, plasma, projector, monitor, printer, touch screen, or other now known or later developed display device. The display 27 receives RGB or other color values and outputs an image. The image may be gray scale or color image. The image represents the region of the patient scanned by the beamformer and transducer 14.

The processor 24 is a digital signal processor, a general processor, an application specific integrated circuit, field programmable gate array, control processor, digital circuitry, analog circuitry, graphics processing unit, combinations thereof or other now known or later developed device for implementing calculations, algorithms, programming or other functions. The processor 24 operates pursuant to instruction provided in the memory 18 or a different memory.

The processor 24 receives flow data from the filter 20, flow estimator 22, spatial filter 28, and/or scan converter 29. In one embodiment, the processor 24 implements one or more of the algorithms, acts, steps, functions, methods or processes discussed herein, by processing the data and/or controlling operation of other components of the system 10. Additional or multiple processors may be used to implement various aspects of the algorithms.

The processor 24 determines display values for each location in a plane from flow data distributed three-dimensionally. The plane corresponds to a two-dimensional image region. The display values are determined from statistics associated with the flow data in the neighboring volume, such as an at least three-by-three-by-three voxel region in the volume. Rather than mere interpolation from four surrounding values for rendering along view lines, the processor 24 determines each flow value from flow data over a broader region. Alternatively, smaller volume neighborhoods, areas, or lines for the kernel may be used. Display values are determined from the statistics.

The processor 24 causes generation of an image as a two-dimensional image representing a plane or as representation rendered from a volume from a viewing direction. For two-dimensional imaging, the flow or color Doppler display values may be overlaid or combined with a B-mode image representing a same plane in the volume.

The instructions for implementing the processes, methods and/or techniques discussed above are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

What is claimed:
1. A method for two-dimensional flow imaging in medical diagnostic ultrasound, the method comprising:
acquiring flow data comprising velocity, energy, or variance, the flow data representing a plurality of different planes around and including a first plane of an object, the different planes including the first plane comprising scan planes;
determining flow values comprising velocity, energy, or variance, the flow values determined for the first plane as a function of the flow data for the plurality of different planes, wherein determining the flow values comprises calculating, for each of a plurality of locations in the first plane and not for the other planes of the plurality of different planes, a statistic from the flow data for a surrounding three-dimensional region and determining the flow value for each of the locations as a function of the respective statistic, the statistic for velocity, energy, or variance being of the velocities, energies, or variances, respectively, for the surrounding three-dimensional region based on a kernel centered at each location in the first plane without placement of the kernel as centered on the other planes of the plurality of different planes; and
generating a flow image representing flow in a two-dimensional region corresponding to the first plane, the flow image being a function of the flow values and being a two-dimensional image of the two-dimensional region without displaying flow values or flow data for the other planes of the plurality of different planes.

2. The method of claim 1 wherein the first plane comprises a center plane of the different planes.

3. The method of claim 1 wherein acquiring the flow data comprises scanning a plurality of times and estimating velocities for the different planes from echoes responsive to the scanning.

4. The method of claim 1 wherein acquiring the flow data comprises transmitting a beam covering at least sixteen distinct receive lines and receive beamforming along the at least sixteen distinct receive lines in response to the beam, the at least sixteen distinct receive lines comprising lines in each of the different planes.

5. The method of claim 1 wherein the different planes are spaced apart in an elevation dimension, the first plane having azimuth and range extent, further comprising:
filtering the flow data at least across the elevation dimension.

6. The method of claim 1 wherein the statistic comprises a maximum, a mean, a standard deviation, a weighted maximum, directional information, or combinations thereof, and wherein the flow values comprise the statistic, a weighted sum of the flow data and the statistic, the flow data, or a second value depending on a threshold applied to the statistic, or combinations thereof.

7. The method of claim 1 wherein generating the flow image comprises generating a color flow image.

8. The method of claim 1 wherein generating the flow image comprises overlaying the flow image on a two-dimensional B-mode image.

9. In a non-transitory computer readable storage medium having stored therein data representing instructions executable by a programmed processor for flow imaging in medical diagnostic ultrasound, the storage medium comprising instructions for:
simultaneously acquiring, in response to one transmission, spatial samples of an object, the spatial samples distributed in a volume including at least parts of multiple slices, the different slices comprising scan slices;
repeating the acquiring at different times;
estimating color Doppler parameter values from the spatial samples acquired at the different times, the color Doppler parameter values representing the at least parts of the multiple slices;
combining the color Doppler parameter values for the multiple slices into a two-dimensional representation, wherein combining comprises calculating, for each of a plurality of locations in a first plane and not for other planes of the multiple slices, a statistic from the flow data for a surrounding three-dimensional region, and determining the color Doppler parameter value for each of the locations as a function of the respective statistic, the statistic for velocity, energy, or variance being of velocities, energies, or variances, respectively, for the surrounding three-dimensional region based on a kernel centered at each location in the first plane without placement of the kernel as centered on the other planes; and
generating an image as a function of the combined color Doppler parameter values and being a two-dimensional image of the two-dimensional region without displaying flow values or flow data for the other planes.

10. The non-transitory computer readable storage medium of claim 9 wherein the two-dimensional representation spatially corresponds to a middle one of the multiple slices.

11. The non-transitory computer readable storage medium of claim 9 wherein the one transmission comprises a broad beam sized to insonify at least sixteen receive lines, the spatial samples being along the receive lines, and wherein the color Doppler parameter values comprise Doppler velocity values.

12. The non-transitory computer readable storage medium of claim 9 wherein the statistic comprises a maximum, a mean, a standard deviation, a weighted maximum, directional information, or combinations thereof, and wherein the color Doppler parameter value comprises the statistic, a weighted sum of the flow data and the statistic, the flow data or a second value depending on a threshold applied to the statistic, or combinations thereof.

13. The non-transitory computer readable storage medium of claim 9 wherein the image comprises two-dimensional B-mode information combined with the combined color Doppler parameter values, the two-dimensional B-mode information and the combined color Doppler parameter values being at different locations within the image.

14. A system for flow imaging in medical diagnostic ultrasound, the system comprising:
a transducer;
a beamformer operable to scan with the transducer;
a Doppler estimator operable to estimate Doppler data for a volume from information obtained by the scan;
a processor operable to determine a display value for each location in an image from Doppler data distributed three-dimensionally in an at least three-by-three-by-three region in the volume, wherein the processor is operable to determine, for each location in a plane and not for the other planes in the Doppler data distributed three-dimensionally, a statistic of the Doppler data in the corresponding at least three-by-three-by-three region and determine the display value as a function of the statistic, the statistic for the Doppler data being of the Doppler data for a surrounding three-dimensional region based on a kernel centered at each location in the plane without placement of the kernel as centered on the other planes; and
a display operable to display the image being a two-dimensional image of the two-dimensional region without displaying flow values or flow data for the other planes.

15. The system of claim 14 wherein the image comprises a two-dimensional B-mode and color flow image representing the plane in the volume.

16. The system of claim 14 wherein the beamformer is operable to transmit a beam covering at least sixteen distinct receive lines and receive along the at least sixteen distinct receive lines in response to the beam, the at least sixteen distinct receive lines comprising lines in the volume and the Doppler data representing points along the receive lines.

17. The system of claim 14 wherein the Doppler data represents the other planes in the volume.

* * * * *